US006972566B2

(12) United States Patent
Guthausen et al.

(10) Patent No.: US 6,972,566 B2
(45) Date of Patent: Dec. 6, 2005

(54) METHOD AND APPARATUS FOR DETERMINING THE FAT CONTENT

(75) Inventors: Gisela Guthausen, Rheinstetten (DE); Arne Kasten, Karlsruhe (DE)

(73) Assignee: Bruker BioSpin GmbH, Rheinstetten-Forchheim (DE)

( * ) Notice: Subject to any disclaimer, the term of this patent is extended or adjusted under 35 U.S.C. 154(b) by 0 days.

(21) Appl. No.: 10/764,981

(22) Filed: Jan. 26, 2004

(65) Prior Publication Data

US 2004/0164736 A1 Aug. 26, 2004

(30) Foreign Application Priority Data

Jan. 28, 2003 (DE) ................................ 103 04 184

(51) Int. Cl.[7] ................................................ G01V 3/00
(52) U.S. Cl. ...................................... 324/307; 324/309
(58) Field of Search ................................ 324/307, 309, 324/306, 312, 314, 300, 318, 319, 322

(56) References Cited

U.S. PATENT DOCUMENTS

| | | | | |
|---|---|---|---|---|
| 3,109,986 A | * | 11/1963 | Woessner | 324/319 |
| 4,477,777 A | * | 10/1984 | Gordon | 324/300 |
| 5,317,262 A | * | 5/1994 | Moonen et al. | 324/309 |
| 5,594,336 A | * | 1/1997 | Gullapalli et al. | 324/309 |
| 5,739,688 A | | 4/1998 | Krieg | |
| 5,798,643 A | * | 8/1998 | Werthner | 324/309 |
| 6,147,492 A | * | 11/2000 | Zhang et al. | 324/309 |

FOREIGN PATENT DOCUMENTS

| | | | |
|---|---|---|---|
| DE | 41 33 643 | C1 | 10/1991 |
| DE | 195 11 835 | A1 | 10/1996 |
| WO | WO 99/54751 | A1 | 10/1999 |
| WO | WO 01/92908 | A1 | 12/2001 |

OTHER PUBLICATIONS

Bl,ü,mler, P. et al., “Spatially Resolved Magnetic Resonance”, Wiley-VCH, 1998, pp. 195-209.

Callaghan, Paul T., “Principles of Nuclear Magnetic Resonance Microscopy”, Oxford Science Publications, Clarendon Press, 1991, pp. 162-169, 330-367, 371-417 and 478-482.

* cited by examiner

*Primary Examiner*—Louis Arana

(57) ABSTRACT

A description is given of a method for determining the content of a first component of a sample, which first component provides a first NMR signal and has a first self-diffusion coefficient $D_1$, the sample additionally containing at least one further component which provides a further NMR signal and has a larger self-diffusion coefficient $D_2$, in particular for determining the fat content of a hydrous sample, with the aid of a low-resolution nuclear magnetic resonance (NMR) pulse spectrometer, the sample being excited by a radio-frequency (RF) excitation pulse and being exposed to a magnetic gradient field and to a sequence of further refocusing RF pulses for generating spin echo signals, the spin echo signals being detected and their amplitude values being determined, from which a value for the content of the first component of the sample is determined. The magnetic gradient field is not switched off during the sequence of further refocusing RF pulses.

16 Claims, 2 Drawing Sheets

METHOD AND APPARATUS FOR DETERMINING THE FAT CONTENT

CROSS REFERENCE TO RELATED APPLICATION

The present application claims priority of German patent application 103 04 184.2, filed on Jan. 28, 2003.

BACKGROUND OF THE INVENTION

The invention relates to a method for determining the content of a first component of a sample with the aid of a low-resolution nuclear magnetic resonance pulse spectrometer.

The invention in particular relates to a method for determining the content of fat in a hydrous sample.

The invention in particular relates to a method for determining the content of a first component of a sample which first component provides a first NMR signal and has a first self-diffusion coefficient $D_1$, the sample additionally containing at least one further constituent, which provides a further NMR signal and has a larger, in particular significantly larger self-diffusion coefficient $D_2$, with the aid of a low-resolution nuclear magnetic resonance (NMR) pulse spectrometer, the sample being excited by a radio-frequency (RF) excitation pulse and being exposed to a magnetic gradient field and to a sequence of further refocusing RF pulses for generating spin echo signals, the spin echo signals being detected and their amplitude values being determined, from which a value for the content of the first component of the sample is determined.

The invention furthermore relates to a low-resolution NMR pulse spectrometer, which, in particular, is set up for carrying out the said method, having an apparatus for generating RF transmission pulses, an apparatus for receiving NMR signals, an apparatus for generating a magnetic gradient field and also a computer for driving the said apparatuses.

Determining the fat content by means of a low-resolution NMR pulse spectrometer with a magnetic field strength of at most about 1 Tesla and average homogeneity of about $10^{-5}$ over the sample volume and thus a proton resonant frequency of less than about 50 MHZ, e.g. the MINISPEC from the company BRUKER, is made more difficult in products with a high water content owing to the superposition of water signal and fat signal since, given relatively high water content, the contribution of the water surpasses that of the fat. The determination is possible in a simple manner only in high-resolution NMR apparatuses, which are generally much too expensive for this application, e.g. in foodstuffs chemistry.

One possibility for arriving at acceptable results even at low resolution consists in predrying the samples before the NMR measurement, whether it be in a drying oven or chemically, as described e.g. in DE 41 33 643 C1. Reference is explicitly made to the entire contents of this document.

WO 99/54751 A1 and also WO 01/92908 A1 describe NMR pulse methods in which not only the different relaxation times $T_2$ of water and fat but also the different self-diffusion coefficient is utilized in order to arrive at a statement about the pure fat content. The entire contents of both documents are incorporated by reference in the disclosure of the present application.

The basis of these two documents is the so-called PFGSE method (pulsed field gradient spin echo; or else for short: PGSE), which is known per se from textbooks (e.g. P. T. Callaghan: Principles of Nuclear Magnetic Resonance Microscopy, Oxford Science Publications, Clarendon Press, Oxford 1991, in particular pages 162–169, 330–367, 371–417 and 478–482 therein).

The core of the PGSE method is illustrated in FIG. 2 of WO 99/54751 A1. After a 90° excitation pulse, a relatively strong magnetic field gradient is switched on and off again. As a result, the magnetic field, which is initially constant over the sample, becomes space-dependent, which, depending on the location, leads to different precession frequencies of the protons in water (and also the fat) molecules and to corresponding dephasing. In contrast to the fat molecules, the free water molecules then move very rapidly through diffusion and change their location.

A subsequent 180° pulse inverts the precessing nuclear magnetizations. The repeated switching-on of the gradient pulse which is identical in terms of intensity and time duration is thus suitable per se for completely rephasing the dephasing again, i.e. the effects of the two gradient pulses cancel one another out. This also applies to a good approximation to immobile molecules or the proton magnetization thereof. However, the mobile water molecules have appreciably changed their location through diffusion between dephasing and rephasing gradient pulses, so that the subsequent spin echo is weakened and no longer contains a water signal at all at sufficiently strong gradients. The different diffusion coefficient of fat molecules and water results in a discrimination possibility and thus a possibility for determining the fat content of a sample, even in an inhomogeneous magnetic field.

This dependence, as is known per se, can be tracked as a function of the gradient strength and/or the echo times and the incoming parameters such as self-diffusion coefficient and $T_2$ can be determined. In particular, it is possible to completely suppress the water component in the measurement signal and thus arrive at a pure fat measurement. It is precisely for water suppression purposes that PGSE has been used for a long time in NMR.

WO 99/54751 A1 additionally proposes following the PGSE step with further 180° pulses and measuring, without gradients, further spin echoes for $T_2$ determination and a corresponding correction (FIG. 4 therein).

In WO 01/92908 A1 this is modified to the effect that identical gradient pulses are switched between all the 180° pulses of a spin echo train in each case before and after the spin echo (see FIG. 2 therein). This corresponds to a PGSE-CPMG spin echo train (see page 166 of the book by Callaghan). The amplitudes of the spin echoes then decay both through $T_2$ and through self-diffusion. At sufficiently strong gradients, even the first spin echo no longer contains a water signal, and a back extrapolation of the amplitude decay should yield the pure fat signal.

The method disclosed in WO 01/92908 A1 permits the fat content to be determined from a spin echo train in a measurement after a single excitation. It can therefore be faster than previous pulse methods for determining the fat content in foodstuffs.

However, the method still has drawbacks.

It requires a precise gradient power supply unit for generating the corresponding gradient pulses, which, moreover, for their part start eddy currents in the apparatus, which eddy currents may impair the measurement.

It furthermore requires the weighing of the samples, since the extrapolated amplitude is dependent on the sample quantity.

SUMMARY OF THE INVENTION

Therefore, there is still the need for a simpler method and a corresponding apparatus. Therefore, the invention is based on the object of providing a simpler method of the type mentioned in the introduction and a corresponding apparatus.

According to a first aspect of the invention a method for determining the content of a first component of a sample with the aid of a low-resolution nuclear magnetic resonance (NMR) pulse spectrometer is provided, said first component having a first self-diffusion coefficient $D_1$, and providing a first NMR signal, said sample additionally containing at least one further component having a further self-diffusion coefficient $D_2$ larger than said first self-diffusion coefficient $D_1$ and providing a further NMR signal, comprising the steps of exciting said sample by a radio frequency (RF) excitation pulse exposing said sample to a magnetic gradient field and exposing said sample to a sequence of further re-focusing RF pulses for generating spin echo signals, wherein said magnetic gradient field is not switched-off during said sequence of further re-focusing RF pulses, detecting said spin echo signals and determining amplitude values of said spin echo signals, and determining a value for said content of said first component of said sample from said amplitude values of said spin echo signals.

With regard to the method mentioned in the introduction, the object is achieved by virtue of the fact that the magnetic gradient field is not switched off during the sequence of further refocusing RF pulses. The object is achieved by virtue of the fact that a departure is made from the schemes that are expedient at high resolution and in the imaging area, to be precise use is made of a gradient but not a PFGSE method, and that the magnetic field gradient is not pulsed during the spin echo train, but rather is present statically.

In order to avoid weighing, preferably at least one point is measured at an early point in time of the free induction decay.

According to a second aspect of the invention a low-resolution NMR pulse spectrometer is provided, comprising an apparatus for generating a magnetic field, an apparatus for generating RF transmission pulses, an apparatus for receiving NMR signals, an apparatus for generating a magnetic gradient field and a computer for driving the said apparatuses, wherein said computer is programmed for carrying out and said apparatuses are configured for carrying out a method for determining the content of a first component of a sample with the aid of a low-resolution nuclear magnetic resonance (NMR) pulse spectrometer.

With regard to the low-resolution NMR pulse spectrometer mentioned in the introduction, the object is achieved by virtue of the fact that the computer is programmed for carrying out the method according to the invention and the apparatuses are configured accordingly.

As a result, the requirements made of the power supply unit are reduced and eddy currents are not obtained.

BRIEF DESCRIPTION OF THE DRAWINGS

The invention is explained in more detail below with reference to the drawing, in which.

DETAILED DESCRIPTION OF PREFERRED EMBODIMENTS

Figure 1:
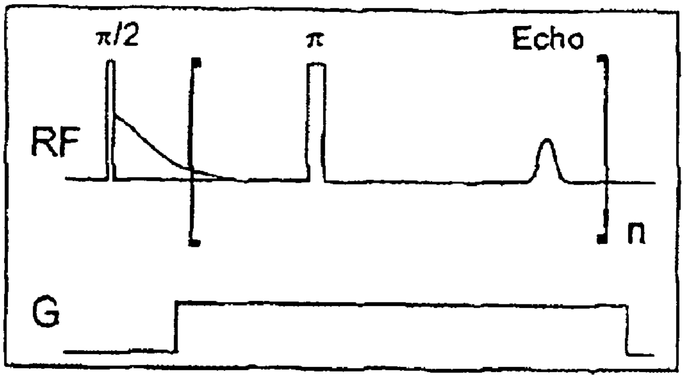
FIG. 1 shows a pulse sequence for measuring the fat content by utilizing the diffusion processes. The gradient is switched after the measurement of part of the free induction decay and before the first refocusing pulse.

Experiments have shown that it is possible to hold the required gradient amplitude over the echo train—which, of course, may be smaller than that of the pulse—without resulting in excessive electrical or thermal loading on the gradient system. However, the amplitude of a constant gradient is significantly simpler to hold and to reproduce than that of a pulsed gradient. In contrast to high-resolution spectroscopy, picking up the spin echoes in the presence of the gradient does not constitute a restriction since only the amplitude in each case is of interest. Equally, the 180° pulses and, if appropriate, the excitation pulse may be of sufficiently broadband nature without any problems, so that they capture all the proton frequencies of the bandwidth prescribed by the gradient and the sample range.

In one embodiment of the invention, the gradient is already applied before the excitation pulse of the sequence, generally a 90° pulse. This means that a static gradient is involved for the pulse sequence.

Since the method is not concerned with quantitatively determining a diffusion constant, but only with reliably back extrapolating a sequence of decreasing echo amplitudes relative to t=0 or obtaining a measure of the fat content from the echo amplitudes, ultimately all that is important is a sufficient magnetic field inhomogeneity over the measurement volume, and not a spatially exactly linear profile of the magnetic field. Since the gradient, as explained, is permitted to be static, it is not absolutely necessary to apply a gradient by means of gradient coils operated by a power supply, rather it is also possible to generate a static field inhomogeneity in a different way, e.g. by means of additional ferromagnetic or permanent-magnetic shim elements which may be fitted to the magnet or to a sample holder, or else by displacing the sample from the magnetic field centre of the magnet. This measure may be implemented once before a measurement series for fat determination and the apparatus may subsequently be set up again for the customary measurements in the homogeneous field. Moreover, the direction of the gradient field is not fixed, but rather may be chosen freely.

In a preferred embodiment, the sample is situated in the customary homogeneous field and the gradient is switched on only after the excitation pulse. This has the advantage that a few measurement points of an FID (free induction decay) may also be measured between the excitation pulse and the switching-on of the gradient, the back extrapolation of which measurement points to t=0 yields a value for the overall signal, i.e. water plus fat (plus, if appropriate, further proton signal components with short relaxation times). As a result, it is possible not only to determine the fat in a sequence, but either to determine the fat and water altogether or, depending on the type of sample, at least the proportion of the fat signal in the overall signal.

The measurement is generally evaluated on the basis of stored values of calibration samples of the same type as the measurement sample, as is known per se.

Typical values for the measurements are magnetic field strengths of between 0.176 T and 1.409 T corresponding to Larmor frequencies of the protons of 7.5 MHz to 60 MHz. The gradient strength used is usually between 0.1 and 0.2 T/m, the repetition time until the next 90° RF excitation pulse is about 2 s, the echo time is 8 ms and the sample quantities are approximately 3 $cm^3$ or 0.5 g. The number of accumulated scans usually lies between 8 and 16. In the foodstuffs sector, typical samples are sauces, dressings, fat-water emulsions such as mayonnaises, margarines, etc.; meat and dairy products are also conceivable. Of interest in the oil industry are rock samples with oil and water proportions (recently also in road surfaces, keyword freezing).

The invention also relates to a low-resolution NMR pulse spectrometer which is set up for carrying out the method according to the invention. In particular, this relates to the programming of one of the variants according to the invention of the spin echo sequence including the required bandwidth of the pulses, the provision of the gradient or a device for displacing or for positioning the measurement sample outside the field centre and, if appropriate, the measurement and back extrapolation of the FID and also the corresponding evaluation software in the computer of the spectrometer.

The devices of the spectrometer, in particular the devices for generating the gradient field, may encompass the variants described further above. The use of actively screened gradient coils is preferred. This essentially eliminates an interaction between the gradient field and the spectrometer magnet, in particular with pole shoes. Therefore, there is no longer the same extent of heating, magnetization reversal processes and eddy currents in the magnet structures (pole shoes) which generally decrease in an uncontrolled manner and multiexponentially with very long time constants and can corrupt the measurement. In particular if the gradient field is switched on only after the excitation pulse, the residual disturbing influence of this switching process is thus also largely eliminated.

The arrangements according to the invention can be combined with shim arrangements known per se or be integrated into them.

Essential elements of the spectrometer are the magnet, the sample head equipped with the possibility for generating gradient fields, the electronic units for generating the radiofrequency and the gradient. The experiment is controlled by means of a computer.

FIG. 1 diagrammatically shows the sequence of the radiofrequency pulses and the time profile of the gradient. The excitation pulse with angle a of rotation and the refocusing pulses with angle b of rotation generate the echoes to be measured or the amplitudes thereof. In a conventional Hahn echo method, a=p/2 and b=p pulses are used. However, the method also works as a general multiecho pulse sequence in which the phases of the pulses and the pulse lengths are adapted to the respective requirements.

Figure 2:
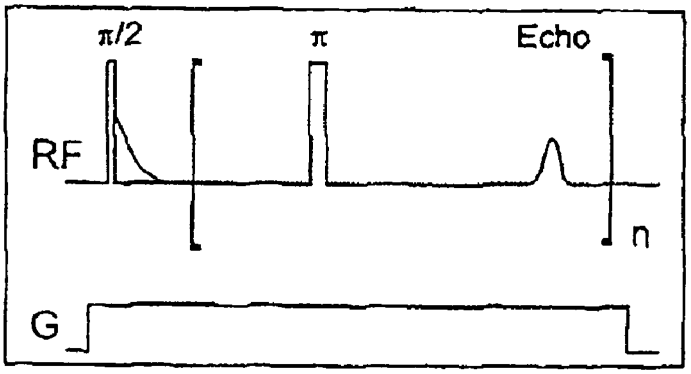
FIG. 2 shows a pulse sequence for measuring the fat content, in which case, in contrast to FIG. 2, the gradient is already switched before the excitation pulse.

FIG. 2 illustrates a variant of the principle: in order to avoid the switch-on effects of the gradient pulses, the gradient is switched on before the sufficiently broadband excitation pulse, so that the magnetization evolution takes place in a magnetic field that scarcely changes with respect to time and all the echoes can be measured under constant refocusing conditions. The gradient may also be present permanently as a genuinely static gradient.

Figure 3:
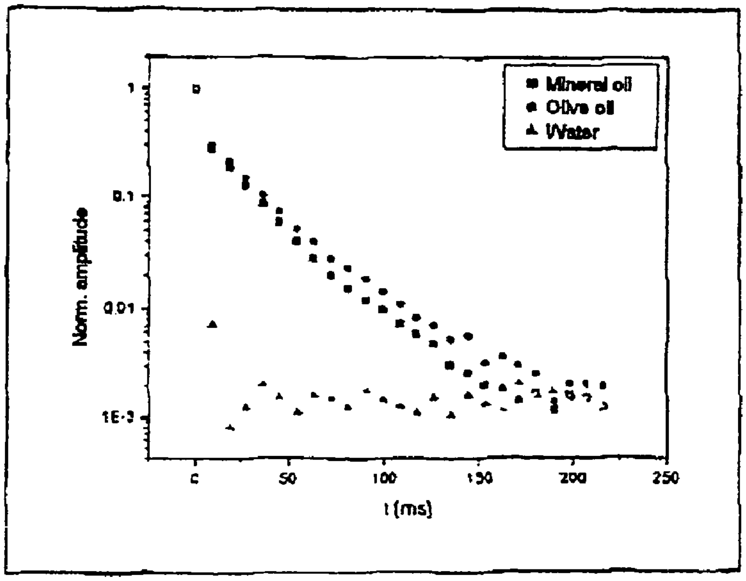
FIG. 3 shows NMR signals corresponding to the pulse sequence from FIG. 3.

FIG. 3 illustrates signals of water and two types of oil logarithmically as a function of the measurement time t in order to demonstrate the principle of the measurement. The water signal decays in the static gradient rapidly on account of the larger diffusion constant, whereas the oil signals are longer to detect. It can also be seen that the two oils differ slightly in terms of relaxation and diffusion. Adaptation of an exponential decay function permits the determination of the oil fraction by extrapolation to t=0. The first measurement point corresponds to the overall signal.

Figure 4:
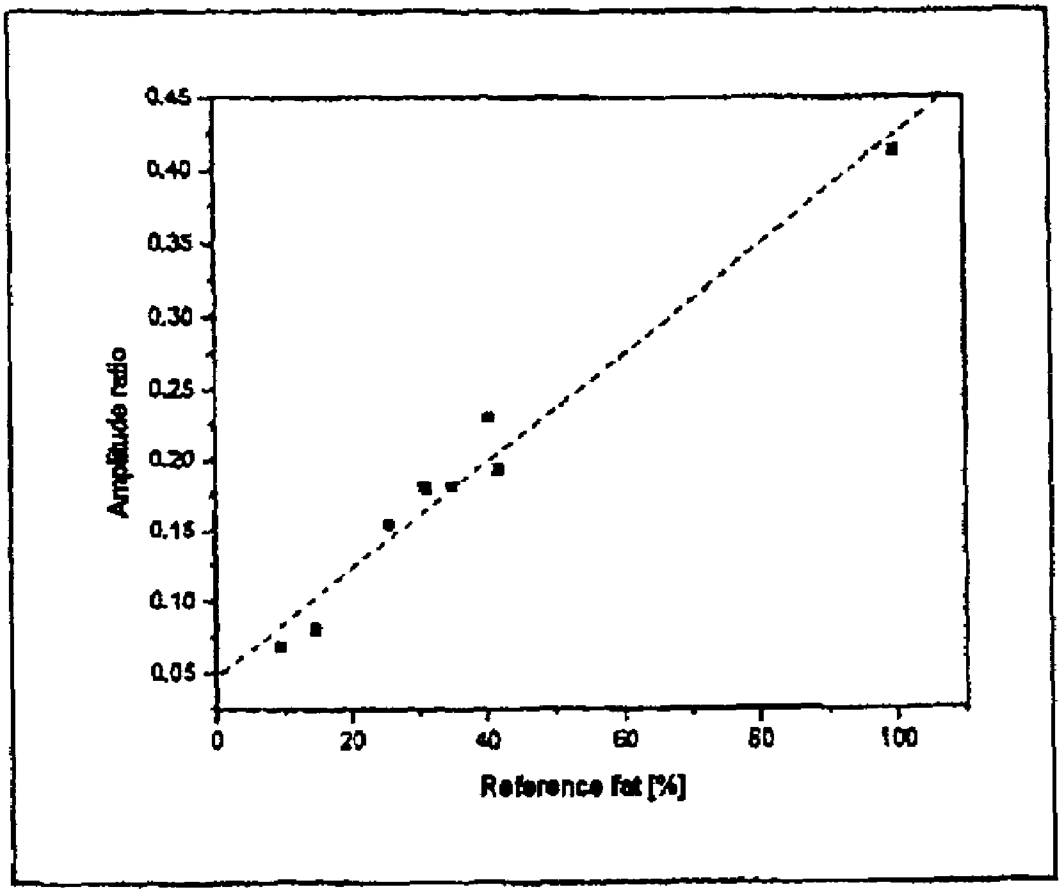
FIG. 4 shows a correlation of the NMR amplitude ratio of diverse water-fat mixtures with a reference fat value.

FIG. 4 shows an exemplary correlation diagram on different fat-water mixtures, as may be obtained from measurements analogous to those illustrated in FIG. 3. Commercially available sauces which are highly inhomogeneous in terms of their structure due to additions were used for these measurements. The NMR amplitude ratio is plotted against the fat reference. These reference values were determined by wet-chemical methods. Forming the ratio of the echo amplitude extrapolated to t=0 to the amplitude of the FID affords the possibility of determining fat without knowledge of the sample weight. Typical sample quantities lie in the range of 0.5 to 0.6 g, but are dependent on the measuring arrangement, specifically the sample head used, and may therefore be varied. Larger sample quantities, primarily in the case of structurally inhomogeneous samples, permit a representative sampling and thus a more reliable measurement. In this case of the sauces, the measurement parameters are: gradient strength G=0.1 T/m, repetition time 8 s, echo time 8 ms, pulse length of the 90° RF excitation pulse 2.5 $\mu$s, dead time before the beginning of the data acquisition 7 $\mu$s. The number of echoes measured was 24. A correlation with the fat reference is exhibited. The correlation coefficient is 0.985 in the case of this measurement. It is determined by the quality of the back extrapolation and of the fat composition, which determines the reliability of the modelling of the decay curve. In the case of complicated fat composition, therefore, the evaluation may be altered to the effect that a direct amplitude ratio is used and the extrapolation is dispensed with.

It goes without saying that the abovementioned features can be used not only in the respective combination but also in other combinations or by themselves, without departing from the scope of the present invention.

What is claimed is:

1. A method for determining the content of a first component of a sample with the aid of a low-resolution nuclear magnetic resonance (NMR) pulse spectrometer, said first component having a first self-diffusion coefficient $D_1$ and providing a first NMR signal, said sample additionally containing at least one further component having a further self-diffusion coefficient $D_2$ larger than said first self-diffusion coefficient $D_1$ and providing a further NMR signal, comprising the steps of:

exciting said sample by a radio frequency (RF) excitation pulse, exposing said sample to a magnetic gradient field and exposing said sample to a sequence of further re-focusing RF pulses for generating spin echo signals, wherein said magnetic gradient field is not switched-off during said sequence of further re-focusing RF pulses, detecting said spin echo signals and determining amplitude values of said spin echo signals, and determining a value for said content of said first component of said sample from said amplitude values of said spin echo signals.

2. The method of claim 1, wherein said gradient field is generated at least partially by gradient coils through which current flows.

3. The method of claim 1, wherein said gradient field is generated at least partially by at least one of ferromagnetic and permanent-magnetic elements.

4. The method of claim 1, wherein said gradient field is generated at least partially by displacing said sample from a homogeneity region of a magnet of said NMR pulse spectrometer.

5. The method of claim 1, wherein said magnetic gradient field also acts during said RF excitation pulse.

6. The method of claim 1, wherein said magnetic gradient field is switched-off during said RF excitation pulse.

7. The method of claim 1, wherein at least one measurement point of a free induction signal (FID) of said sample is measured after said RF excitation pulse.

8. The method of claim 7, wherein said at least one measurement point is measured in the absence of said magnetic gradient field.

9. The method of claim 8, wherein an overall proton signal containing proportions of said first component and said at least one further component of said sample is determined from said FID.

10. The method of claim 1, wherein at least one measurement point of a free induction signal (FID) of said sample is measured after said RF excitation pulse, and wherein an overall proton signal containing proportions of said first component and said at least one further component of said sample is determined from said FID.

11. The method of claim 1, wherein a gradient strength of said magnetic gradient field is set in such a way that, at the instant of the first spin echo, the NMR signal contribution of said at least one further component in said sample is essentially suppressed by diffusion under the action of said gradient.

12. The method of claim 1, wherein said content of said first component of said sample is obtained by back extrapolation of an amplitude decrease of said spin echo signals until the instant of excitation.

13. The method of claim 1, wherein said sample is a hydrous sample, and wherein said first component is fat.

14. The method of claim 13, wherein said at least one further component is water.

15. A low-resolution NMR pulse spectrometer comprising an apparatus for generating a magnetic field, an apparatus for generating RF transmission pulses, an apparatus for receiving NMR signals, an apparatus for generating a magnetic gradient field and a computer for driving said apparatuses, wherein said computer is programmed for carrying out and said apparatuses are configured for carrying out a method for determining the content of a first component of a sample with the aid of a low-resolution nuclear magnetic resonance (NMR) pulse spectrometer, said first component having a first self-diffusion coefficient $D_1$ and providing a first NMR signal, said sample additionally containing at least one further component having a further self-diffusion coefficient $D_2$ larger than said first self-diffusion coefficient $D_1$ and providing a further NMR signal, comprising the steps of:

exciting said sample by a radio frequency (RF) excitation pulse exposing said sample to a magnetic gradient field and exposing said sample to a sequence of further re-focusing RF pulses for generating spin echo signals, wherein said magnetic gradient field is not switched-off during said sequence of further re-focusing RF pulses, detecting said spin echo signals and determining amplitude values of said spin echo signals, and determining a value for said content of said first component of said sample from said amplitude values of said spin echo signals.

16. The low-resolution NMR pulse spectrometer of claim 15, wherein said apparatus for generating a magnetic gradient field comprises actively shielded gradient coils.

* * * * *